(12) United States Patent
Zimmerman

(10) Patent No.: US 11,961,167 B2
(45) Date of Patent: Apr. 16, 2024

(54) METHODS AND SYSTEMS FOR VISUALIZING SOUND AND HEARING ABILITY

(71) Applicant: Jay Alan Zimmerman, New York, NY (US)

(72) Inventor: Jay Alan Zimmerman, New York, NY (US)

(*) Notice: Subject to any disclaimer, the term of this patent is extended or adjusted under 35 U.S.C. 154(b) by 94 days.

(21) Appl. No.: 17/549,269

(22) Filed: Dec. 13, 2021

(65) Prior Publication Data

US 2022/0189084 A1    Jun. 16, 2022

Related U.S. Application Data

(60) Provisional application No. 63/124,390, filed on Dec. 11, 2020.

(51) Int. Cl.
| | |
|---|---|
| *G06T 11/20* | (2006.01) |
| *A61B 5/00* | (2006.01) |
| *A61B 5/12* | (2006.01) |
| *G06T 3/40* | (2006.01) |

(52) U.S. Cl.
CPC ............ *G06T 11/206* (2013.01); *A61B 5/121* (2013.01); *A61B 5/743* (2013.01); *G06T 3/40* (2013.01); *G06T 11/203* (2013.01); *A61B 2503/40* (2013.01)

(58) Field of Classification Search
CPC ....... G06T 11/206; G06T 3/40; G06T 11/203; G06T 2200/24; A61B 5/121; A61B 5/743; A61B 2503/40; G16H 15/00; G16H 50/50
See application file for complete search history.

(56) References Cited

U.S. PATENT DOCUMENTS

| | | | |
|---|---|---|---|
| 2007/0135730 A1* | 6/2007 | Cromwell | G16H 50/20 600/559 |
| 2009/0136050 A1* | 5/2009 | Hakansson | H04R 25/70 381/60 |
| 2010/0020988 A1* | 1/2010 | McLeod | H03G 5/025 381/107 |
| 2011/0109798 A1* | 5/2011 | McReynolds | H04S 7/30 348/E7.001 |
| 2011/0142272 A1* | 6/2011 | Takagi | H04R 25/70 381/321 |
| 2013/0108095 A1* | 5/2013 | Wei | H04R 25/70 381/320 |

(Continued)

OTHER PUBLICATIONS

Muller et al., Short-Time Fourier Transform and Chroma Features, International Audio Laboratories Erlangen (Year: 2015).*

(Continued)

*Primary Examiner* — Michael Le

(57) ABSTRACT

A computer-implemented method of visualizing hearing ability, comprising acquiring, by one or more processors, audio data, generating, by the one or more processors, a hearing ability visualization with the audio data for display, wherein the hearing ability visualization includes a graphical element, a horizontal axis representing volume, and a vertical axis representing frequency, the graphical element being positioned relative to the horizontal axis such that volume is louder closer to the graphical element and quieter further from the graphical element.

20 Claims, 13 Drawing Sheets

(56) References Cited

U.S. PATENT DOCUMENTS

| | | | | |
|---|---|---|---|---|
| 2014/0050334 A1* | 2/2014 | Antonellis | ............. | H03G 5/165 381/98 |
| 2014/0272883 A1* | 9/2014 | Pardo | ...................... | G09B 5/04 434/319 |
| 2018/0144524 A1* | 5/2018 | Lotto | ..................... | G06T 11/60 |
| 2020/0382868 A1* | 12/2020 | Felton | .................. | G06F 3/0482 |

OTHER PUBLICATIONS

Papadopoulos et al., CyberSeer: 3D Audio-Visual Immersion for Network Security and Management, Proceedings of the 2004 ACM workshop on Visualization and data mining for computer security, Oct. 2004, pp. 90-98 https://doi.org/10.1145/1029208.1029223 (Year: 2004).*

James Jerger, et al., Why the Audiogram is Upside-down, hearingreview.com, pp. 1-12 (2013).

Donald A. Vogel, et al., The Clinical Audiogram, Its History and Current Use, Communicative Disorders Review, vol. 1, No. 2, pp. 81-94 (2007).

* cited by examiner

METHODS AND SYSTEMS FOR VISUALIZING SOUND AND HEARING ABILITY

CROSS-REFERENCE TO RELATED APPLICATIONS

This application claims priority to U.S. Provisional Application 63/124,390 filed Dec. 11, 2020, which is incorporated by reference in its entirety.

FIELD OF THE PRESENT DISCLOSURE

The present disclosure relates to visualizations of sound and hearing ability in a variety of fields and formats, and, more particularly, to hearing test audiograms and other related audiological visualizations commonly appearing on audiology forms and generated by audiometric equipment and other computerized devices.

BACKGROUND

When a person is attempting to understand their hearing ability they often take a hearing test and receive a data visualization called an audiogram. For over 100 years, audiologists and other medical personnel have generated visualizations of hearing ability using an audiogram grid that maps sound pitches/frequencies on the horizontal axis with the highest pitches on the far right and sound volumes/decibels on the vertical axis with the loudest volumes at the bottom, and with information for both ears often overlapping each other on the same grid with the results for the left ear marked as an X and the results for the right ear marked as an O, as shown in FIG. 1.

This basic configuration was first conceived in the late nineteenth century, formally adopted during the 1949 International Congress of Audiology in London, and standardized by the American Standards Association (ASA). The world-wide standard for audiograms today retains this basic configuration, with the exact details set by the International Standards Organization-American National Standards Institute (ISO-ANSI) since Nov. 1, 1967. For more information about the history of traditional and standardized audiograms, see the articles "The Clinical Audiogram: Its History and Current Use" and "Why The Audiogram Is Upside-Down."

However, most people cannot comprehend their hearing ability as visualized on a traditional audiogram because the resulting image and orientation directly conflicts with their mental conception of sound. For example, in real life, people generally refer to high pitches as "high" and visually see them as high on a music score but on a traditional audiogram they are shown on the far right. Similarly, in real life, people generally understand that generating loud sounds requires large actions and see this "loud=large" relationship visualized on audio equipment volume meters and in personal device volume graphics but the traditional audiogram represents loud as the smallest, lowest point near the bottom of the graph. In addition, pitches people generally consider to sound "low" such as tones from an electric bass or a tuba are not typically graphed on the standardized audiogram of today, which causes confusion for example if an audiologist tells a person they do not have "low" frequency hearing when in actuality the pitches the audiologist is referring to are only visually "low" on the traditional audiogram and may be in actuality so high in pitch they can only be played by flutes or sung by sopranos.

The reason the standardized audiogram uses these confusing display limits and convoluted orientation methods is because the guiding design principle was not to reveal a person's hearing ability but rather to compare one person's hearing perception against a fictional "normal" person's hearing perception and then define the difference as "loss" in levels of mild, moderate, severe, and profound abnormality.

To emphasize the severity of such a "loss" the standardized audiogram of today causes further confusion by measuring sound volumes not in actual decibels, or "sound pressure level" decibels (dB SPL) but in what are called "hearing level" decibels (dB HL), a non-scientific measurement fabricated by adding extra "bonus" decibel amounts to the actual decibel measurements of sound pressure at particular frequencies for the sole purpose of visualizing "normal" human perception of quiet as a flat, straight line.

In actuality, human perception of quiet volumes over the entire frequency spectrum of human hearing has been determined by multiple studies to be a curve. Visualizing hearing ability using "hearing levels" also means that a person cannot compare the volumes and decibel numbers appearing on their audiogram to any volumes and decibel numbers used in noise warnings, science, or any field other than audiology, not even the decibel numbers appearing in the specifications of their consumer audio equipment and hearing amplification devices.

A person's comprehension of their hearing "loss" is further obscured by the traditional audiogram because graphing hearing on it creates images, and over time these images have been given nonsensical names divorced from real life experiences, causing doctors to inform patients that they have a "ski slope hearing loss" or a "cookie bite hearing loss" or are unable to hear in the zone of the "speech banana." None of these terms connect to any relatable hearing experience in real life because they refer solely to images resulting from drawings of hearing ability on the traditional audiogram grid.

Lastly, because the traditional, standardized audiogram orientation is designed to emphasize various degrees of "loss" from the straight line for "normal" every person defined as having less than "normal" hearing is given a negative perspective on their hearing ability in both imagery and language, causing depression and shame as well as confusion about whatever hearing ability they may still possess.

In sum, the standardized audiogram used throughout the world today, as shown in FIG. 1, visualizes the left ear as an X and the right ear as an O because the left side is for low pitches and the right side is for high pitches, while the high part of the chart shows quiet volumes and the low part shows loud volumes, and all the notes on the lower half of a piano have been left off of the chart and therefore are not tested. Because this convoluted and confusing visualization system has a negative focus, is disconnected from the average person's understanding of sound, and is very limited in scope, approximately 90% of the world's 460 million people with limited hearing do not understand their hearing ability and as a result do not obtain any technology or treatments to help them hear more.

Therefore, a need exists for systems and methods that can transform audiometric hearing test data into positive and intuitively understood visualizations of hearing ability that not only empower people through greater comprehension of the type of hearing they have, but also aid in their decision-making about potential treatments and assistive technologies through further visualizations of the benefits of those treatments and technologies.

A need also exists for systems and methods that can provide a uniform yet adaptable underlying structure for hearing ability visualizations that may be used for a multiplicity of purposes, such as to layer and compare an infinite number of patient's hearing test results for statistical analysis, to visualize the historical progression of a person's changing hearing ability over several years, to visualize all sound-generating things in an individual's life and how those sounds may or may not be perceived by the individual, to visualize helpful additional data and graphics using a variety of sound wave measurement methods, and for many other known and unknown uses including analyzing and comparing human ability results with the hearing ability of animals or studying the capabilities of sound-perceiving devices for infrasound and ultrasound applications.

SUMMARY

Therefore implementations described and claimed herein overcome the foregoing problems through new and novel methods and systems for combining multiple types of sound and hearing data from multiple sources into a unified, intuitively understood, visualization of any entity's hearing ability herein referred to as a "field of hearing" or "hearing field." Embodiments of the present disclosure relate to, among other things, systems and methods for computer-implemented two-dimensional and three-dimensional hearing field visualizations of all entities, including individual humans, multiple humans, animals, and any sound-perceiving and sound-generating devices.

For example, when utilizing an exemplary embodiment, and according to aspects of the present disclosure taught herein, a person taking a hearing test may see a virtual representation of themselves on a graphical interface, represented as a human figure in the center of a stereo visualization of their field of hearing. Using the methods and systems described herein, this field of hearing may be defined and readily understood to be comprised of information about their hearing perception. Information about their hearing perception on the left side of their body may appear on the visual left of the human figure while information about their hearing perception on the right may appear on the visual right side, creating an experience similar to that of looking in a mirror. The total width of their hearing field may be displayed on the horizontal plane as a distance measured in quantities of loudness with dangerously loud volumes appearing as dangerously close to the human figure's ears and the quietest volumes they can perceive as further away from the human figure on both the right and left to visually establish the outer limits of their field of hearing. Similarly, the total height of their hearing field on the vertical plane may be revealed through graphical means to be encompassing all the various pitches/frequencies they can perceive, from the highest pitches/frequencies appearing far above the human figure's head to the lowest frequencies appearing far below the human figure's head. The final resulting shape of their hearing field created by plotting their hearing test data as described and graphically linking these data points may then take on various characteristics depending on their hearing ability type. For example, excellent hearing may be shown as a very wide far-hearing shape in contrast to Deaf hearing being shown as an extremely narrow near-hearing shape.

Some embodiments may utilize additional systems and methods disclosed herein to allow a person to visually explore how their personal field of hearing may possibly expand by using particular hearing amplification devices, or how it may contract by wearing particular protective hearing devices, or to explore a variety of scenarios to learn more about the limits of their hearing field and learn, for example, how far away they may place their cell phone and still hear it ring. Scientists, hearing health professionals, manufacturers, researchers, and/or other interested parties may also utilize the disclosed visualization systems and methods for a variety of purposes, for example to study multiple human fields of hearing and layer them, to analyze and compare multiple hearing devices, compare various types of human hearing with types of animal hearing, to monitor infrasound measurements of earthquakes or view potentially damaging ultrasounds in the workplace, or to study various sound-generating objects such as musical instruments.

One aspect of the disclosure provides for a computer-implemented method of visualizing hearing ability, comprising acquiring, by one or more processors, audio data, generating, by the one or more processors, a hearing ability visualization with the audio data for display, wherein the hearing ability visualization includes a graphical element, a horizontal axis representing volume, and a vertical axis representing frequency, the graphical element being positioned relative to the horizontal axis such that volume is louder closer to the graphical element and quieter further from the graphical element. Generating the hearing ability visualization can include plotting a first line intersecting the graphical element and corresponding to a first frequency, and a second line a distance from the graphical element and corresponding to a second frequency, wherein the second frequency is less than the first frequency. The second line may not intersect the graphical element. The graphical element can be placed at a position along the horizontal axis to correspond to a volume level that causes pain to an average human. The audio data can include spatial data, wherein generating the hearing ability visualization includes generating a three-dimensional hearing ability visualization with a third axis corresponding to a distance from the graphical element using the spatial data. The graphical element can be a representation of a human figure. The vertical axis can be a piano keyboard in which each note of the piano keyboard is in vertical alignment with its corresponding frequency value in hertz. The horizontal axis can be one of a physical distance, sound pressure level decibels, or hearing level decibels. The method can further comprise zooming on a portion of the hearing ability visualization. The method can further comprise labelling the hearing ability visualization with a label corresponding to a type of hearing ability based on the audio data.

Another aspect of the disclosure provides for a computer-implemented method of visualizing hearing ability, comprising acquiring, by one or more processors, a first audio data corresponding to a first ear of a patient and a second audio data corresponding to a second ear of a patient, and generating, by the one or more processors, a hearing ability visualization with the first and second audio data for display, wherein the hearing ability visualization includes a graphical element, a horizontal axis representing volume, and a vertical axis representing frequency, the first and second audio data being along a same side of the graphical element. Generating the hearing ability visualization can include plotting a first line intersecting the graphical element and corresponding to a first frequency, and a second line a distance from the graphical element and corresponding to a second frequency, wherein the second frequency is less than the first frequency. The second line may not intersect the graphical element. The graphical element can be placed at a position along the horizontal axis to correspond to a volume level that causes pain to an average human. The first and second audio data can include spatial data, wherein generating the hearing ability visualization includes generating a three-dimensional hearing ability visualization with a third axis corresponding to a distance from the graphical element using the spatial data. The graphical element can be a representation of a human figure. The vertical axis can be a piano keyboard in which each note of the piano keyboard is in vertical alignment with its corresponding frequency value in hertz. The horizontal axis can be one of a physical distance, sound pressure level decibels, or hearing level decibels. The method can further comprise zooming on a portion of the hearing ability visualization. The method can further comprise labelling the hearing ability visualization with a label corresponding to a type of hearing ability based on the first and second audio data.

This summary of the present disclosure introduces a selection of concepts in a simplified form that are further described below in the detailed description. This summary is not intended to identify key features or essential features of the claimed subject matter, nor is it intended to be used to limit the scope of the claimed subject matter. Other objects and advantages of the present disclosure will be readily apparent to those skilled in the art upon viewing the drawings and reading the detailed description hereafter.

BRIEF DESCRIPTION OF THE DRAWINGS

By way of example, there are shown and described several exemplary embodiments of this present disclosure. As will be realized, the present disclosure is capable of other embodiments, and its several details are capable of modification in various, obvious aspects all without departing from the present disclosure. Accordingly, the drawings and descriptions will be regarded as illustrative in nature and not as restrictive. In the drawings.

DETAILED DESCRIPTION

Figure 1:
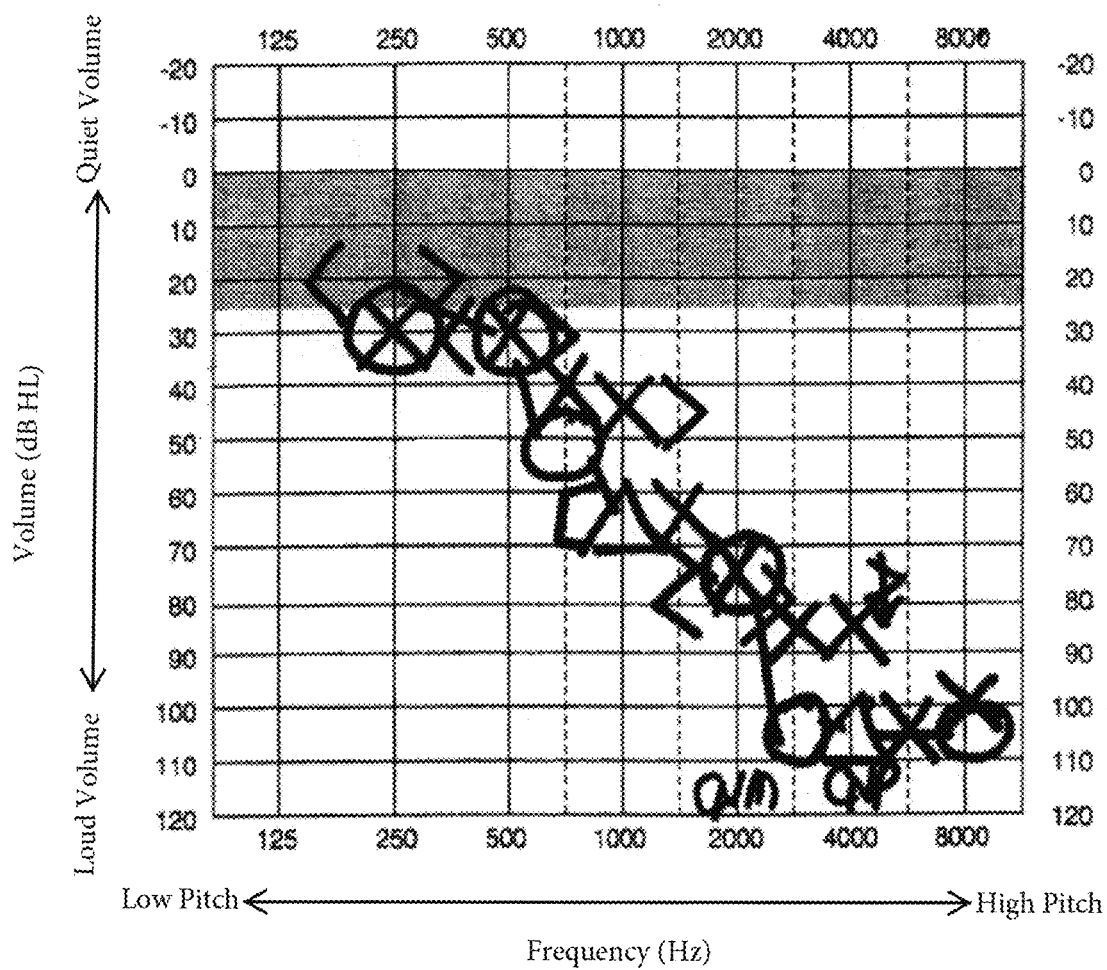
FIG. 1 is a scan of an ISO-ANSI standard audiogram prepared by an audiologist that displays hand-drawn audiometric data for one person.

The following description is disclosed to enable audiologists, audiometric equipment manufacturers, medical form designers, scientists, and others skilled in the art to make and use the present disclosure in conjunction with the specific needs of their field and devices.

While the present disclosure is described herein with reference to illustrative embodiments for particular applications, it should be understood that embodiments of the present disclosure are not limited thereto. Other embodiments are possible, and modifications can be made to the described embodiments within the spirit and scope of the teachings herein, as they may be applied to the above-noted field of the present disclosure or to any additional fields in which such embodiments would be of significant utility. For example, embodiments described herein can be used with any good and/or service that can be represented digitally.

In the detailed description herein, references to "one embodiment," "an embodiment," "an example embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

These embodiments, which are also referred to herein as "examples," are described in enough detail to enable those skilled in the art to practice the present disclosure. The embodiments may be combined, other embodiments may be utilized, or structural, logical and electrical changes may be made without departing from the scope of the present disclosure. The following detailed description is, therefore, not to be taken in a limiting sense, and the scope of the present disclosure is defined by the appended claims and their equivalents.

In this document, the terms "a" or "an" are used, as is common in patent documents, to include one or more than one. In this document, the term "or" is used to refer to a nonexclusive or, unless otherwise indicated. Furthermore, all publications, patents, patent documents, whitepapers, and technical papers referred to in this document or in the attached appendices are incorporated by reference in their entirety herein, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

Therefore, the present disclosure is not intended to be limited to the particular embodiments shown and described but is to be accorded the widest scope consistent with the principles and features disclosed herein.

Figure 6:
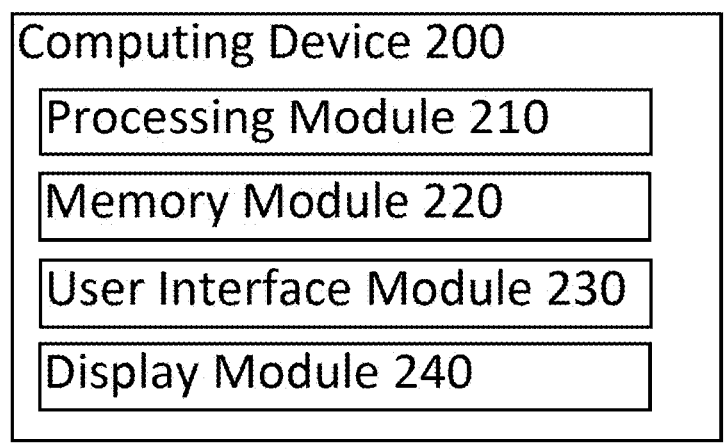
FIG. 6 is an example computing device in accordance with aspects of the disclosure.

To begin, a system for transforming hearing test data into a hearing ability visualization, herein referred to as a "field of hearing" and "hearing field", may acquire the needed audiometric or other audio data. Note that audio data can include data related to sound as well as data related to the perception of sound. Acquisition may include queries of an existing audiometric database, input from audiometric equipment during an audiology exam, user data transmitted from online hearing tests, manual data entry via a computerized submission form, or through any other means such as scanning a historical paper audiogram as seen in FIG. 1 into a computer device, such as computing device 200, as shown in FIG. 6 and discussed further below.

Figure 2:
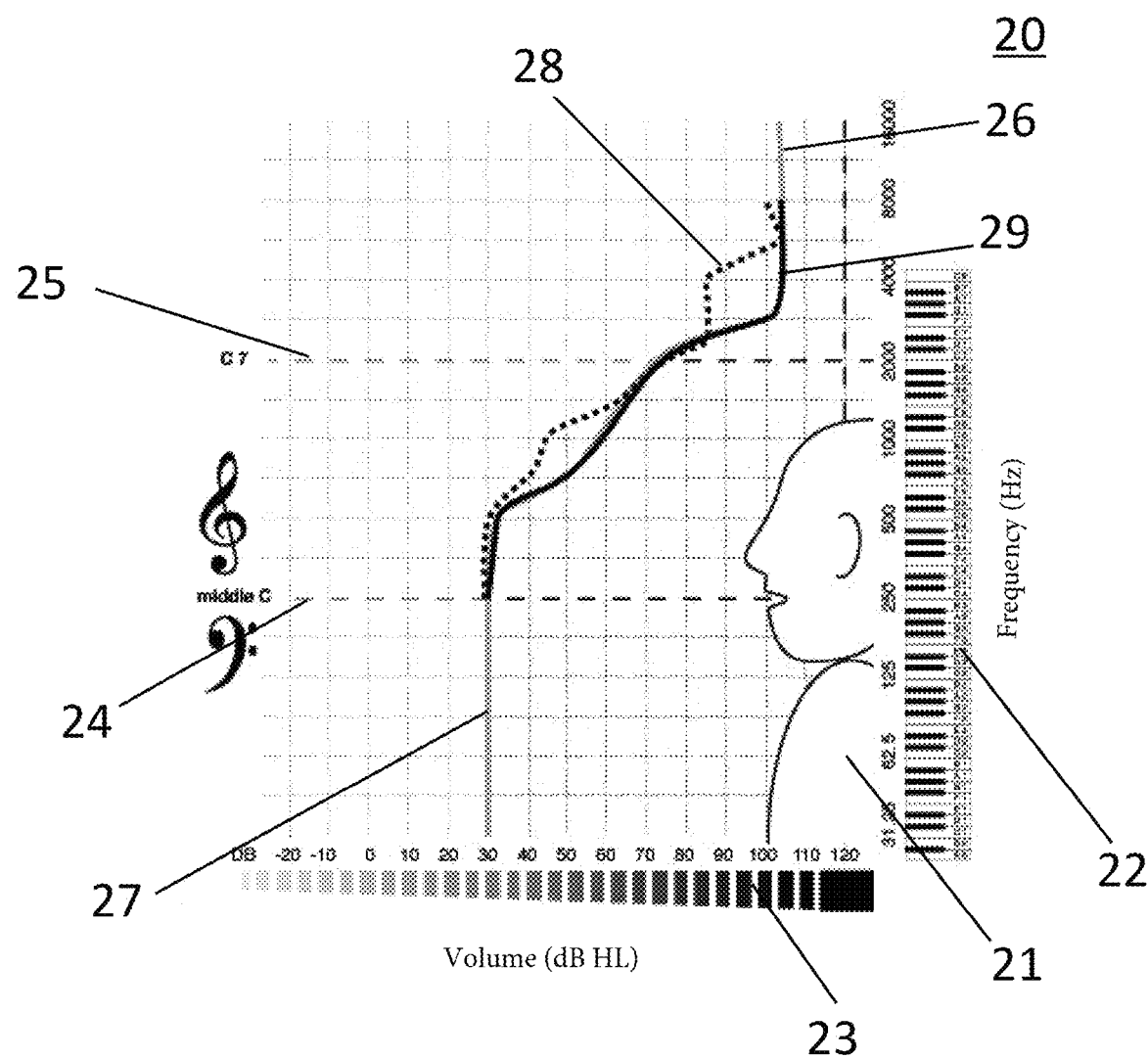
FIG. 2 is a hearing ability visualization in a mono/overlay configuration that visualizes the same audiometric data appearing on the scanned audiogram in FIG. 1 in the style of a side-view image.

To process and render the visualization, a default or user-selected presentation mode may be chosen such as the mono configuration illustrated in FIG. 2, a stereo widescreen configuration such as seen in FIGS. 3-5 and 7-12, a polar plot mode, a 3D virtual reality mode, augmented reality overlay mode, or any other relevant display mode configuration.

Figure 3:
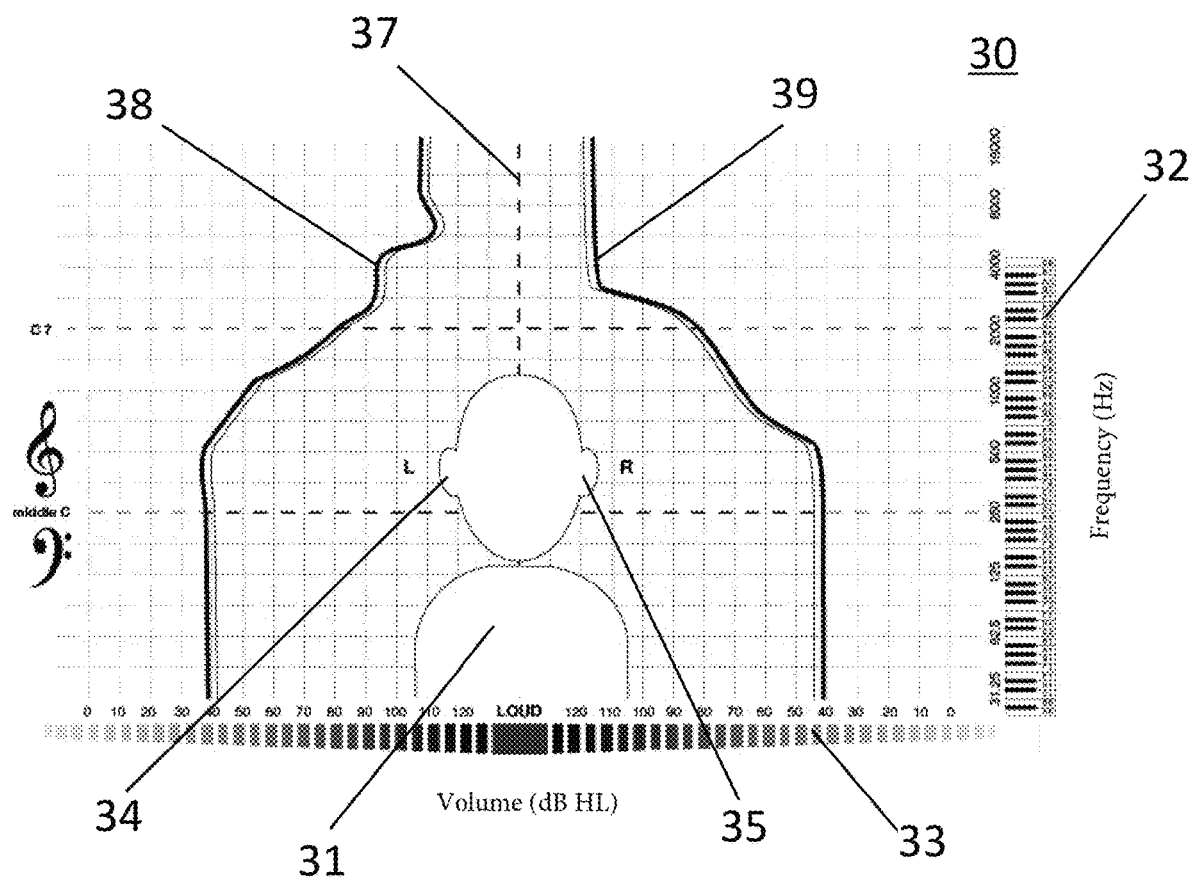
FIG. 3 is a hearing ability visualization in a stereo configuration utilizing the same audiometric data found in FIGS. 1-2 in the style of a front view, widescreen-style, image.

A default or user-selected measurement mode may also be chosen, such as displaying frequencies in logarithmic quantities in hertz and volumes in logarithmic quantities of decibels using "hearing level" decibels as seen in FIGS. 1-3, "sound pressure level" decibels as seen in FIGS. 4-5 and 7-12, and discussed further below, phons, or any other sound measurement system including physical distance illustrations using inverse ratio calculations of sound decay over distance.

For clarity, the term "sound pressure level decibels" in this document and abbreviated as "dB SPL" refers to soundwave intensity as a result of movement of energy from one air molecule to another. Whereas the term "hearing level decibels" abbreviated as "dB HL" refers to a perception of loudness caused by that soundwave intensity with the SPL decibels numbers being altered by adding variable numbers of dB to the actual measured intensity so that the perceived loudness appears as a flat line at the quietest level heard by the average young person. These additions range from the smallest value of 7.5 dB added to zero at 1000 and 1500 hertz, to the largest value of 45 dB added to zero at 250 hertz. Hearing level decibels were adopted by audiologists and physicians in the 1960s, but create a picture of hearing that is not representative of the actual physics of sound and the fact that humans have variable sensitivity to sound based on the frequency of the sound, which is perceived as pitch.

In addition, a default or user-selected display zoom level may be chosen, for example from a smallest zoomed-in view of a single frequency and single volume level, to the human view of the spectrum of human hearing from 20 hertz to 20,000 hertz and the human volume tolerance levels from 0 dBL to 120 dBL, and/or zoomed out to display the entire spectrum of frequencies and volume levels possible in the known universe. For example, FIG. 1 shows the limited view of the traditional audiogram while the other illustrated embodiments use a range of 20 hertz to 20,000 hertz.

Upon obtaining any one data point in terms of the quietest volume that the person or entity can perceive on a particular pitch/frequency in a single ear, this data point may appear on the graphical interface as a fixed plot point in space at the appropriate horizontal distance from a virtual representation of the person's or entity's location and at a vertical height in relationship to the person's or entity's ears or other sound-perceiving component. The horizontal distance being the dynamic range in volumes of loudness that the person/entity can perceive through that ear/receiver on that particular pitch with the quietest volume visualized as furthest from that ear/receiver and dangerously loud volumes visualized as directly next to that ear/receiver. The receiver can be any means of perceiving sound, such as a microphone or the like. Meanwhile the vertical placement may show how "high" or "low" the pitch/frequency is in relationship to the dominant frequencies found in the tones of human speech, with tones that are commonly impossible to produce with human vocal cords shown as high above the head of the virtual representation of the person, while extremely low tones are shown far below the head. In the case of non-human entities this vertical placement of high and low may be centered according to the range of frequencies such entity perceives.

As more data points about the person's or entity's hearing ability are acquired, these individual plot points may similarly fill in vertically and horizontally on the left and right sides of their virtual representation in the stereo widescreen mode in accordance with the left ear/receiver and right ear/receiver perception, the pitch/frequency data points, and volume/decibel data points, until a sufficient number have been plotted and/or estimated in order to create a visualization of a complete field of hearing. These data points may then be linked using a variety of graphical means to delineate the zone of hearing ability versus the zone outside of hearing ability. In three dimensional embodiments, additional spatial data points regarding hearing perception at the front and back of the person/entity's location may be acquired and visualized accordingly.

After completing a field of hearing visualization, additional methods and systems are herein disclosed that may enable the display of helpful graphical icons. For example, a person may wish to understand how their hearing ability relates to their perception of music, and so musical icons such as music clefs, dynamics, and piano keyboards may be displayed as seen in the illustrated embodiments. Images or icons of particular musical instruments may also be accurately layered on the visualization corresponding to the frequency spectrums and dynamic volume ranges that these elements can produce and/or represent.

Additionally, a person may wish to know more about common sounds in their life or explore how various treatment scenarios may transform their field of hearing. For example, to see how the volume of their cell phone ring tone relates to their hearing ability and how close the phone must be to an ear in order to be perceived with and without assistive devices. To achieve a visualization of this scenario, the estimated decibel level of the cell phone ring tone at the source may be entered and then recalculated in terms of the decibel level over quantities of distance using sound decay calculations. This would convert the horizontal axis of volume into a logarithmic display of physical distance, so that an image or graphic representing a cell phone may then appear on a person's hearing field visualization and be dragged horizontally by the user until finding a physical distance where the decibel volume of the cell phone ring tone overlaps with their hearing field. The cell phone image may also be placed vertically in alignment with the pitch/frequency of the ring tone if the tone is known and constant. In other cases, a person may wish to debate the benefits of a hearing device or implant, and so the specifications of each device may be acquired and similarly mapped onto the visualization to instantly visualize how such device or implant may alter the person's field of hearing and perception of daily sounds and devices.

As the above describes, the numerous benefits of the present disclosure over prior art include its intuitive, positive, and helpful visualizations that are simultaneously and significantly more accurate and more flexible than a traditional audiogram or other sound visualization systems. The present disclosure's unique organizational system for combining multiple types of sound and hearing data from multiple sources may create a unified and intuitively understood visualization of hearing ability that increases user comprehension, allows for comparison, and supports in-depth and detailed analysis. Providing methods for multiple display options including display of familiar icons and other accurately placed graphical elements such as volume meters and piano keyboards as seen in the illustrations may further aid the viewer in quickly understanding their field of hearing and how it functions in the real world.

Most importantly, the disclosed methods may transform simple plot points and line graphs focused on emphasizing the negatives of "loss" into more positive spatial representations of a person's hearing ability. This new orientation may completely transform how people view and talk about hearing ability. No longer will people need to be defined as having a shameful "loss" that requires "fixing" by medical intervention but rather the existing quantity of their hearing perception will be revealed so that they can choose how to utilize it to maximize their hearing ability and improve their hearing experiences.

Accuracy in measuring both sound and hearing ability may also be significantly improved. Prior art such as FIG. 1 uses "hearing level" decibels which means that a person's perception of sound is compared to a fictional "normal" person's perception of sound and then it quantifies the difference in perceptions as a "loss." This approach measures perception against perception, neither of which is fully verifiable. In stark contrast, the present disclosure, as described further below for FIG. 4, separates the scientific measurement of sound from a person's perception of sound, thus establishing a flexible yet scientific underlying framework for measuring soundwaves in a variety of formats, i.e., traditional decibels, A-weighted decibels, as well as other scientific measurement systems such as phons, and then layers a person's perception of those soundwaves on top of this framework.

Accuracy may also be significantly improved because the present disclosure visualizes "loud" as closest to a person as seen in the illustrations rather than as a flat line at the bottom of a graph as seen in FIG. 1. "Loud" visualized as "close" not only represents how humans experience loud in real life but more importantly visualizes extreme loudness as a fixed element common to all humans no matter what hearing ability they have. This is because at extreme volume levels loud/intense soundwaves can cause eardrum rupture and even death even if one does not hear the sound at all. And many studies have shown that painfully loud volume levels are relatively consistent for all humans of every hearing type, while perceptions of quiet are extremely variable. With "loud" visualized as a fixed point, the present disclosure may also accurately show sound volumes as physical distance from a person/entity because sound volume decays at a constant rate over distance.

In comparison to prior methods, the method of the present disclosure is significantly more adaptable because it uses an expandable underlying framework that can show the totality of sound volumes and sound pitches found in the universe and utilize multiple measurement methods for visualizing them, as well as simultaneously display the field of hearing of an infinite amount of people, animals, and non-human devices as well as sounds outside of human perception such as infrasound and ultrasound.

Referring now to the figures, FIG. 1 is a scan of a completed traditional audiogram as it was given to a patient using prior methods. This image clearly demonstrates how confusing, limiting, and negative prior methods of visualizing hearing have been for over 100 years. It uses the current underlying ISO-ANSI standardized graph of displaying volumes/decibels on the vertical axis (or y-axis), ranging from low to high volume, and pitches/frequencies on the horizontal axis (or x-axis), ranging from low to high pitch. As shown, the patient's audiometric data has been hand-drawn with overlapping markings by the audiologist. An "X" denotes hearing data for the left ear and an "O" denotes hearing data for the right ear. A "normal" hearing ability is defined as a straight line at zero "hearing levels" (0 dB HL).

As indicated by the markings, the range of frequencies shown and tested start at 250 Hz and end at 8,000 Hz. As explained previously, this is a limited view of the full potential frequency range of human hearing, which roughly ranges from 20 Hz to 20,000 Hz. Such a limited testing range leaves out the tones of most male voices, several octaves of low notes on the piano, and low sounding musical instruments such as tubas.

The hand-drawn lines of the audiologist that connect the plotted audiometric data and the various marked symbols have been joined together to create an overall downward slope often categorized and called a "ski-slope hearing loss." There are no graphical indications to inform the viewer as to where the remaining hearing ability of the patient appears in relationship to this slope.

In stark contrast, the exemplary hearing ability visualizations as seen in FIGS. 2-3 use the exact same data points yet are more readily and intuitively understood by the viewer because the imagery and orientation aligns with commonly understood concepts. It will be readily appreciated by the skilled artisan having the benefit of the disclosure herein that an exemplary embodiment need not be limited to the particular graphic design elements shown in these figures, such as fonts, line thicknesses, shading, transparency, icons, and so forth. Various digital embodiments of the present disclosure may also provide the user with the option to turn on and off text elements and graphical elements as desired for greater comprehension, or even to view the embodiments and their elements in a three dimensional format, virtual reality environment, and/or in augmented reality.

For example, FIG. 2 depicts an exemplary hearing ability visualization 20 revealing the system's orientation and method of visualizing hearing data in a mono/overlay display mode. This particular mode might be used by medical professionals as a transitioning step from the traditional audiogram to the full spectrum wide-screen style stereo display mode as seen in FIG. 3, and/or for small medical forms and other uses where display space is limited.

The FIG. 2 hearing ability visualization embodiment is presented in a completed state after the audiometric data in FIG. 1 has been provided to a computing device. FIG. 2 depicts a vertical axis, further clarified by graphical element 22, as representing pitch data (in Hz). Graphical element 22 ranges from high pitch, at the top of the vertical axis, to low pitch, at the bottom of the vertical axis. Volume data (in dB HL) is represented by the horizontal axis, depicted by graphical element 23, ranging from loud volumes at the right end of the axis and quiet volumes at the left end of the axis. Left ear data is represented by the dashed line 28. Right ear data is represented by the solid line 29. In other alternative embodiments, volume can be represented along the vertical axis while the frequency can be represented along the horizontal axis.

As seen in FIGS. 2-5 and 7-12, when utilizing an exemplary embodiment, and according to aspects of the present disclosure taught herein, other graphical elements may be displayed within the visualization, such as element 21. Element 21 can be a human figure, photograph, or other virtual representation of the person or entity. Including a graphical representation of the person or entity being tested may clarify to who/what the field of hearing belongs and help the person being tested better understand the limits of their personal field of hearing.

In this mono/overlay configuration, element 21 is depicted as a human figure represented in a sideview style with only one ear visible. Horizontally, element 21 may be placed as seen in FIGS. 2-12 with the threshold of "quiet" volumes furthest away from the location of element 21 to simulate how quieter sounds generally seem further away in real life and with the threshold of pain intersecting with the human figure's ear to simulate how very loud sounds may seem dangerously close in real life.

Vertically, element 21 may be placed as seen in FIGS. 2-11 so that the frequency of middle C on the piano at roughly 250 hertz passes through the mouth area. This position puts the zone of tonal frequencies heard most often in speech in alignment with the mouth while lower tones produced by male voices and bass singers appear slightly below the mouth and higher tones produced by female voices and sopranos appear slightly above the mouth.

This vertical positioning also puts the very highest pitched non-human sounds, such as the tones that are too high to be produced generally by human vocal cords, high above element 21. Similarly, the very lowest pitched sounds, such as sounds of whales and rumble of earthquakes, may be plotted below element 21. The combined horizontal and vertical positioning of Element 21 places it in the nexus between volume and pitch.

Various graphical elements depicted in FIG. 2 may be turned on and off depending on the selected presentation mode and be utilized to aid comprehension, ground the viewer, and add specificity. For example, the vertical axis can be depicted with a graphical element 22 in the form of a piano keyboard and the horizontal axis can be depicted with a graphical element 23 in the form of a volume meter.

In the exemplary embodiments of herein, the volume meter graphic visually emphasizes loudness by the use of increasing darkness and a growing, slanted shape that doubles as a representation of distance seen in a perspective drawing. In other embodiments, the horizontal axis can be represented by other graphical icons, such as volume icons commonly seen in software, the dynamic markings and crescendos seen in music notation, and volume meters found on audio equipment.

The numerical values for sound intensity in decibels (dB) may be placed in alignment with a volume meter graphic and may range from the threshold of hearing to the threshold of pain. In the exemplary embodiment of FIG. 2 the dynamic range has been quantified using the same "hearing level" (dB HL) that appear on a traditional audiogram, with the quietest being −20 dB HL and the loudest being 120 dB HL. Other embodiments, such as FIG. 4, may use a different metric to quantify loud and quiet volumes, such as the sound pressure decibels (dB SPL) used in science and the recording arts.

When displaying a piano keyboard graphic as a representation of pitch/frequency the various note keys may be orientated in the same manner as the frequency lines as seen in these figures, i.e., with the highest notes near the top of the graph and the lowest notes at the bottom. The note names may also appear on the keys as seen in the figures and range from the lowest note on an 88-key piano (A0) to the highest note on an 88-key piano (C8), as shown on the keys of graphical element 22, in order to aid quick comprehension and home testing. The frequency numbers in hertz may also be placed in alignment with the piano keyboard and the hearing ability visualization grid as seen in these figures. Additional music icons may be displayed for further clarity. For example, FIG. 2 depicts graphical elements as musical symbols, such as a bass clef and a treble clef, and bolded dashed lines appearing at C4 (250 Hz) and C7 (2000 Hz) to divide hearing ability visualization 20 into low, mid, and high frequency bands.

When dividing the vertical axis of frequencies into three frequency bands, they may be referred to as easy-to-understand segments such as the "bass", "treble", and "high-end" in order to utilize terms commonly known in the music and sound recording arts. Those skilled in the art will readily appreciate that in some embodiments the exact location of these divisions may occur at different frequencies and be rendered and highlighted through a variety of different graphic design methods.

The "bass" segment, is represented by the lowest segment of hearing ability visualization 20 below line 24, denoting the line corresponding to "middle C" (or 250 Hz) represents an expansion of the traditional audiogram because most frequencies below 250 Hz are not typically tested or even represented on traditional audiograms. This "bass" segment includes all the pitches/frequencies typically graphed in the bass clef of music notation, sung by bass singers, and played in popular music by the electric bass. In an exemplary embodiment, this section would include all of the lowest notes on a piano and the lowest frequencies humans typically hear and may even include subsonic frequencies.

The middle vertical "treble" segment, is represented by the segment of hearing ability visualization 20 above line 24 and below line 25, the "C7" line (denoting the line corresponding to 2000 Hz) includes the pitches/frequencies typically found in the treble clef of music notation, sung by soprano singers and played by popular instruments such as the violin that often perform the most important melodic elements in music. Most of the sonic elements found in speech are contained within this area as well, such as the vowels and tonal consonants.

The top "high end" segment, represented by the portion of hearing ability visualization 20 above 2000 Hz, also represents an expansion of the traditional audiogram since, in traditional audiograms, frequencies above 8000 Hz are not often tested or even represented. It includes the highest notes on a piano, the dominant frequencies found in the highest consonant sounds in speech such as f, s, th, and extremely high-pitched sounds such as whistles and bird twitters. In an exemplary embodiment, this section may include all the highest frequencies humans typically hear and may even include ultrasonic frequencies heard by animals such as bats and dolphins.

It will be readily appreciated by the skilled artisan having the benefit of the disclosure herein, that some of these graphical elements, or alternative graphical elements, or no graphical elements at all may be included or not included with the hearing ability visualization as desired. For example, there may be no graphical elements 25, 26.

The underlying hearing ability visualization grid of decibels and frequencies may itself be similar to a traditional audiogram's frequency and decibel grid. However, the grid may be expanded as previously explained and with the axis of pitch/frequency moved to the vertical axis so that the highest frequencies on the highest part of the grid. Volumes/decibels may then be moved to the horizontal axis. The grid may also maintain the traditional audiogram's proportional relationship between volume and pitch as seen in the figures, such relationship being one octave on the frequency scale equivalent in span to 20 decibels on the decibel scale. All or none of the underlying hearing ability visualization grid itself need be visible to the viewer, the grid simply serves as a guide for plotting data.

Once all the frequency and decibel values for one or both ears have been plotted and graphically joined, the resulting lines or similar graphical elements may visually represent the outer limits of a person's hearing abilities and visually reduce the space around element 21. For example, in FIG. 2 the threshold lines have been extended with lines 26, 27 at the top and bottom of the plotted frequency data in order to represent an estimation of the person's full hearing ability.

The outer portions of the grid not perceived by the person/entity may be emphasized by lightening those grid portions so as to appear missing. Those skilled in the art will recognize there are a variety of graphical methods to achieve a similar effect, such as using shading or color. In contrast, the inside portion nearer the human figure may remain unchanged, or unshaded, or colored brighter, or through other methods made to look more positive than the portions not perceived. This type of approach will represent in an obvious fashion what hearing ability the person/entity has that may be made use of with amplification technology. This approach may also be used to illustrate what hearing ability may be added with the use of hearing aids, cochlear implants, and other hearing technology by dramatically restoring lightened, shaded, or colored areas.

Turning now to FIG. 3, hearing ability visualization 30 depicts the same audiometric data found in the traditional audiogram of FIG. 1 and the mono/overlay configuration of FIG. 2, except the audiometric data has been transformed into a stereo/widescreen visualization display mode. FIG. 3 is similar to FIG. 2 in most aspects except the left and right ear data are separated out to different areas of hearing ability visualization 30. In particular, right ear data is represented by line 39, to the right of graphical element 31, and left ear data is represented by line 38, to the left of graphical element 31. hearing ability visualization 30 includes a similar vertical axis, represented by graphical element 32, as graphical element 22 of hearing ability visualization 20. Loud volumes are represented along the horizontal axis as being closer to graphical element 31, while quieter volumes are represented as being farther away from graphical element 31.

The left/right stereo orientation has been reinforced by placing the human figure, represented by graphical element 31, in the center of the stereo image in a front-view style so that both ears 34, 35 are visible. The letter "L" represents the left ear 34 and the letter "R" represents the right ear 35. Those skilled in the art will recognize additional methods may be used to clarify which side represents which ear, such as placing the words "LEFT" and "RIGHT" over or under the correct side. In other embodiments, the words and data may also be reversed so that instead of placing left and right on the left and right of the visualization as if looking in a mirror, the left would appear on the right as if looking at someone through a window.

By centering the human figure along the horizontal axis as shown in FIG. 3 and mirroring the left and right decibel sequence of volumes, the loudest volumes may appear directly in the center very close to the ears and the quietest volumes far away, therefore visually replicating the human experience of sound in everyday life. The threshold of pain may be aligned with the human figure's ears so as to make clear that passing this level of sound intensity may be dangerous. Center line 37, rendered in bold and dash, represents the division between left ear and right ear grids.

In FIG. 3, as similarly seen in FIG. 2, the human figure's head may be aligned vertically so that the frequency of middle C on the piano passes through the mouth area, placing the zone of tonal frequencies heard most often in speech in alignment with the mouth. And by sizing the head similarly to FIG. 2, tones that are much higher than human vocal cords typically produce may appear high above the head, out of reach of human ability.

The resulting stereo/widescreen display mode image can resemble a large mirror in which a person may view their entire "field of hearing" in a manner similar to how one understands their field of vision. With this orientation, in combination with the human figure, the concepts of "loud" and "quiet" may become quickly connected with the concepts of near and far. This may make the dynamic ranges of volume more easily understood because they become connected with the concept of distance from a source, such as experienced in real life (e.g., when a car passes by a person).

This process may result in the traditional vertical "hearing loss" images previously called "ski slope", "cookie bite", "corner", and other confusing terms, being transformed into widescreen-style images that represent the listener's hearing thresholds as a reduced personal space as felt in a variety of natural and architectural environments found in real life.

Representing hearing loss as reduced personal space may also help visualize hearing loss as reduced distance from necessary sonic alerts in daily life, such as a knock on the door, ringing phone, or fire alarm. Using these techniques of visual encroachment and reduced visual space may also help patients be more receptive to treatments.

In these examples, the connecting lines between plotted data have been smoothed in order to emphasize the overall results. With advances in hearing test methods, a smoother contour may happen as a natural result of testing more frequencies within a fuller range of frequencies.

Figure 4:
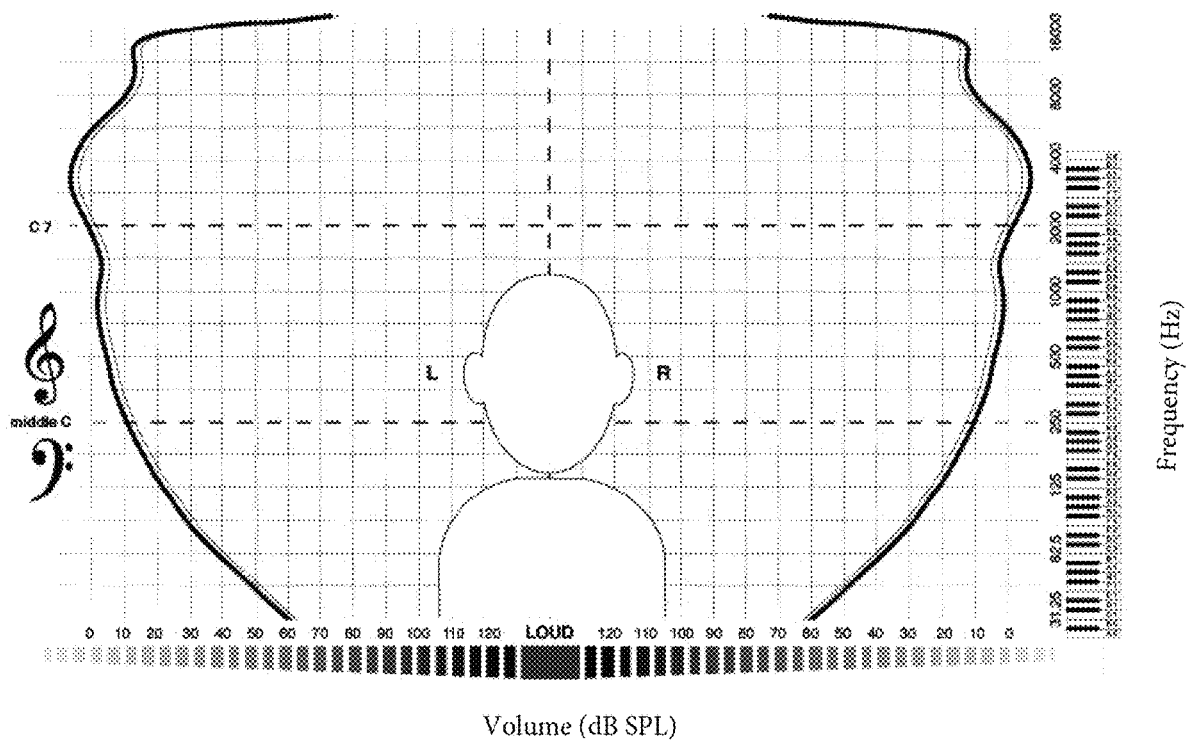
FIG. 4 is a hearing ability visualization of so-called "normal" hearing in a stereo, widescreen configuration but depicted using actual decibels (dB) for the horizontal axis instead of hearing level decibels (dB HL) as shown in FIG. 1 as a straight line at zero dB HL.

Turning now to FIG. 4, hearing ability visualization 40 is similar to hearing ability visualization 30 except the decibels numbers represent sound pressure level decibels rather than the fabricated "hearing level" decibels, as used in FIGS. 1-3. Thus, in FIG. 4 a graphical visualization of the human "normal" threshold of audibility using sound pressure level decibels no longer appears as a straight line as it does on traditional audiograms similar to FIG. 1. Instead it appears curved exactly as it does in numerous scientific studies throughout history that document the thresholds of human hearing, with the exception that instead of appearing as a single horizontal curve it is now a mirrored vertical curve in a stereo/widescreen style display mode. This provides the central human figure with a large range of personal hearing field space, but instead of appearing in an unnatural space between two straight lines, the human figure is in a space that reflects natural environments.

Figure 5:
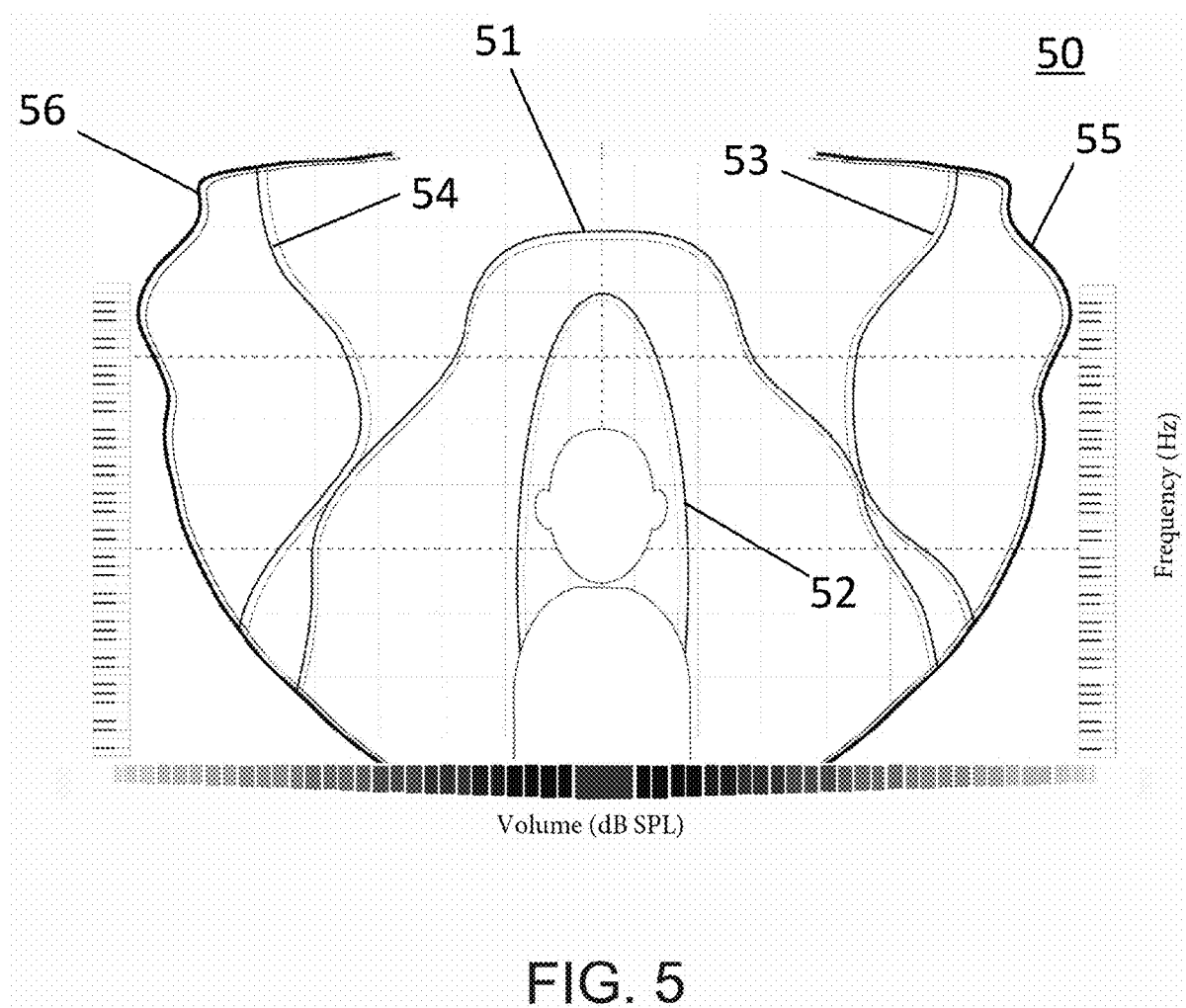
FIG. 5 is a hearing ability visualization in a layered view of multiple human hearing field types, from an excellent far-hearing field to a Deaf near-hearing field in accordance with another aspect of the disclosure.

The present disclosure may also be extremely helpful for exploring assistive listening technologies and various treatments long before needing to make a purchase or undergo surgery. By combining a person's visualized hearing ability with a hearing device capability visualization, one may be able to estimate the expansion or contraction of their hearing field if they choose to use the device. In addition, by layering visualizations of a person's changing hearing ability over time. For example, FIG. 5 retains most display and orientation elements from FIG. 4 while illustrating a display mode of layering multiple human hearing field types in one image, from an excellent far-hearing field to a Deaf near-hearing field. FIG. 5 depicts a layered hearing ability visualization 50, one might show and estimate personal hearing fluctuations over a lifetime. In this example, lines 51, 52, 53, 54, 55, 56 each can depict a hearing ability of one or more patients. Other examples of a layered hearing ability visualization can depict a person born with excellent far-hearing from ages 1-17, their modified hearing field while using hearing protection during loud events, a mild reduction in hearing ages 18-24, moderate/severe reduction to narrow near-hearing ages 25-38, a progression to profoundly deaf ages 39-47, and an expansion of hearing field after cochlear implant surgery ages 48-62. The layered mode may be useful in comparing multiple patient's hearing abilities or for showing a progressively changing hearing field of a single individual over a number of years.

A display mode may include additional exemplary embodiments beyond those illustrated in the figures such as a polar plot mode, a 3D virtual reality mode, augmented reality overlay mode, or any other relevant display mode configuration. A zoom level mode may include additional views from the smallest zoomed-in view of a single frequency and single volume level, to the human view of the spectrum of human hearing from 20 hertz to 20,000 hertz and the human volume tolerance levels from 0 dBL to 120 dBL, or zoomed out to display the entire spectrum of frequencies and volume levels possible in the known universe. A measurement mode may include multiple pitch/frequency display options and multiple volume measurement systems including A-weighted decibels, sound pressure level decibels as seen in FIG. 4, phons, or any other sound measurement system including physical distance illustrations using inverse ratio calculations of sound decay over distance. And optional informational graphic elements may include those described herein, such a piano keyboard, music icons, volume meters, sound generating devices such as cell phones, or any other helpful graphic.

Example Device

With reference to FIG. 6, computing device 200 can be a desktop computer, laptop, smart phone, wearable device, or any other computing device that can generate the hearing ability visualizations as described in this disclosure. Computing device 200 includes a processing module 210, memory module 220, user interface module 230, and display module 240.

Processing module 210 can include a central processing unit (CPU) and a graphics processor. The CPU can manage the overall operations of computing device 200, including executing instructions housed within memory module 200 (e.g., instructions to perform the methods described in this disclosure). The graphics processor can generate graphical displays and/or animation for display on display module 250, such as the hearing ability visualizations as described in this disclosure.

Memory module 220 can include one or more of a non-transitory computer-readable medium or media, a volatile memory unit or units, or a non-volatile memory unit or units. Memory module 220 can include, for example, flash memory and/or NVRAM. Memory module 220 can be embodied as one or more of a hard-drive or memory card, DVDs, CD-ROMs, high-density tape drives, and other types of write-capable or read-only memories. Memory module 220 can include instructions (e.g., a program or application) to be executed by one or more processors, such as the methods described herein. Additionally, memory module 220 can include data to be retrieved, stored or modified by the processors in accordance with the instructions. The instructions can be any set of instructions to be executed directly or indirectly by the processors. For example, the instructions may be stored as computing device code on the computing device-readable medium.

For example, memory module 220 can be a non-transitory computing-device readable storage medium on which computing-device readable instructions of a program are stored, the instructions, when executed by one or more processors, causes computing device 200 to perform a method, such as the methods disclosed herein.

User interface module 230 can include components to receive commands from a user via user inputs and convert them for submission to a given processor in processing module 210. The user inputs may include one or more of a touch screen, keypad, mouse, stylus, microphone, or other types of input devices. For example, user interface module 230 can receive inputs from a user when acquiring audiometric data from a user.

Display module 240 can include a display interface for displaying information on computing device 200. For example, display module 240 can include a screen and the appropriate circuitry and components to display information (e.g., hearing ability visualizations) on that screen.

Computing device 200 can be one device connected to other devices in a system through a communications network in which computing device 200 can execute instructions housed in another computing device of the system. This communications network can be any configuration or protocol enable computing devices, or other electronic devices, such as audiological equipment, to communicate with each other, such as the Internet, Bluetooth™, WiFi, or the like. For example, computing device 200 can be in communication with a server having similar components as computing device 200. The server can be coupled with a database. The server can house similar data and instructions as that stored in memory module 200, such that the processors of processing module 220 can execute instructions and interact with data stored in the server.

It should be understood that the components for computing device 200 described herein are merely exemplary and that there may be more or less components for the operation of computing device 200.

Example Visualizations

In the following FIGS. 7-12, the audiometric data of various audiogram "hearing loss" types have been transformed by the flowchart of FIG. 13 into exemplary hearing ability visualization embodiments of the present disclosure.

Figure 7:
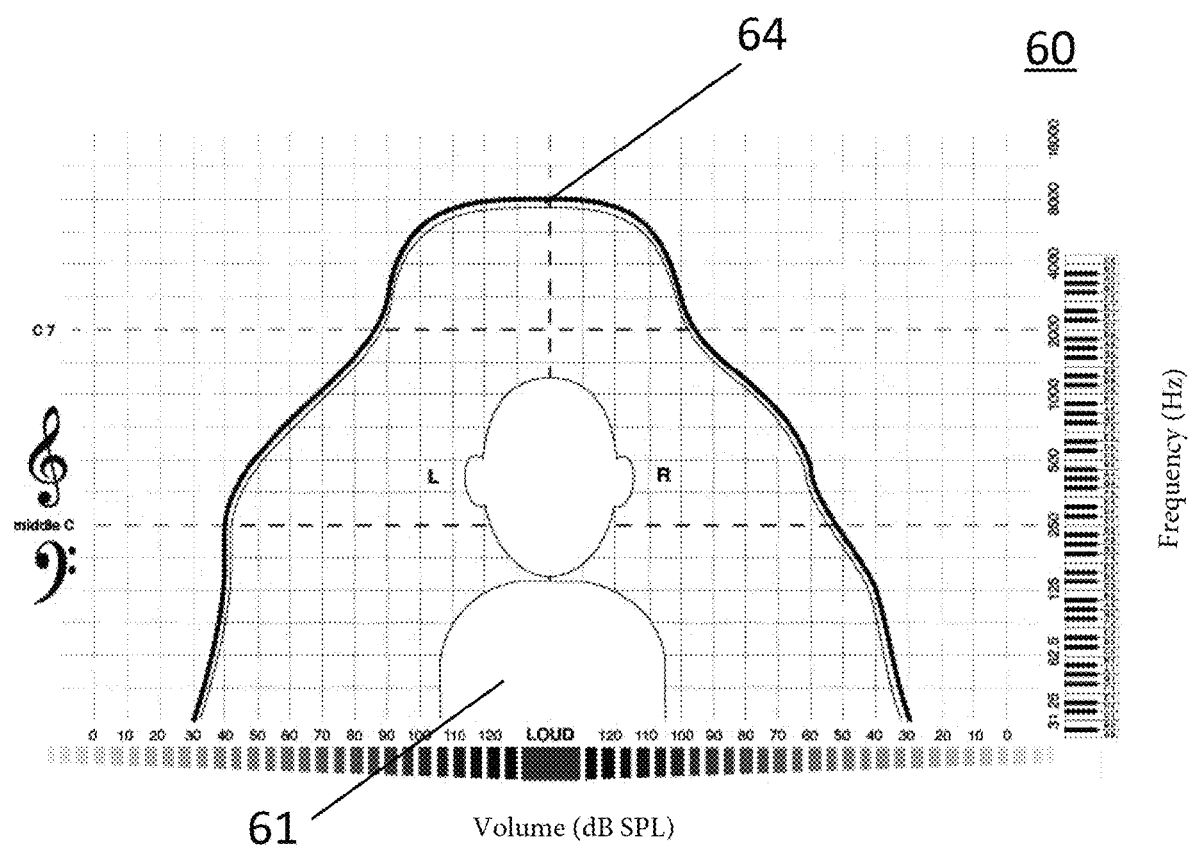
FIG. 7 is a hearing ability visualization that has transformed audiometric data commonly referred to as a "ski slope hearing loss" into an image that may now be referred to as "cave hearing" in accordance with another aspect of the disclosure.

The following examples demonstrate, for example in FIG. 7, how a depressing and confusing "ski slope hearing loss" designed to show relatively no useful hearing remaining on a traditional audiogram may be instantly transformed by a computer into a positive visualization of hearing ability and how this zone of personal hearing ability surrounds the listener in real space. The resulting shape of this field of hearing created by its height, width, and largest areas now resembles a physical space, such as being in a cave. Thus, a "ski slope hearing loss" could now be referred to as "cave hearing" which clearly reveals the person has more ability to perceive lower frequencies than higher frequencies. Since volumes are visually expressed as distance, one could also say they are more "far-hearing" in lower frequencies and more "near-hearing" in high frequencies, and therefore may wish to explore technologies that improve their perception of high frequencies so that they can hear them at a greater distance.

All FIGS. 7-12 use the same stereo/widescreen display mode and sound pressure level decibels (dB SPL) measurement system as seen in FIG. 4 but are visualizations of different audiometric data representing these traditional "hearing loss" types. The data for each has been transformed by the flowchart of FIG. 13 from a standard audiogram orientation into graphical visualizations of exemplary embodiments of the present disclosure. However, it is understood that the mono/overlay type display mode of the exemplary embodiment as seen in hearing ability visualization 20 of FIG. 2 can be used.

The following examples illustrate particular properties and advantages of some of the embodiments of the present disclosure. Furthermore, these are examples of reduction to practice of the present disclosure and confirmation that the principles described in the present disclosure are therefore valid but should not be construed as in any way limiting the scope of the present disclosure.

Example 1

FIG. 7 depicts hearing ability visualization 60 as a graphical visualization that has transformed a commonly called "ski slope hearing loss" into an image similar to walking into a "cave." With the audiometric data for the high frequency limits plotted accurately, there may be readily observed a significantly reduced "ceiling" 64 closing in on the human figure's head. With the side thresholds of volume/decibels also plotted and drawn accurately, the side limits also appear to be closing in on the human FIG. 61, visualizing a much smaller field of hearing and a reduced dynamic range from quiet to loud.

Example 2

Figure 8:
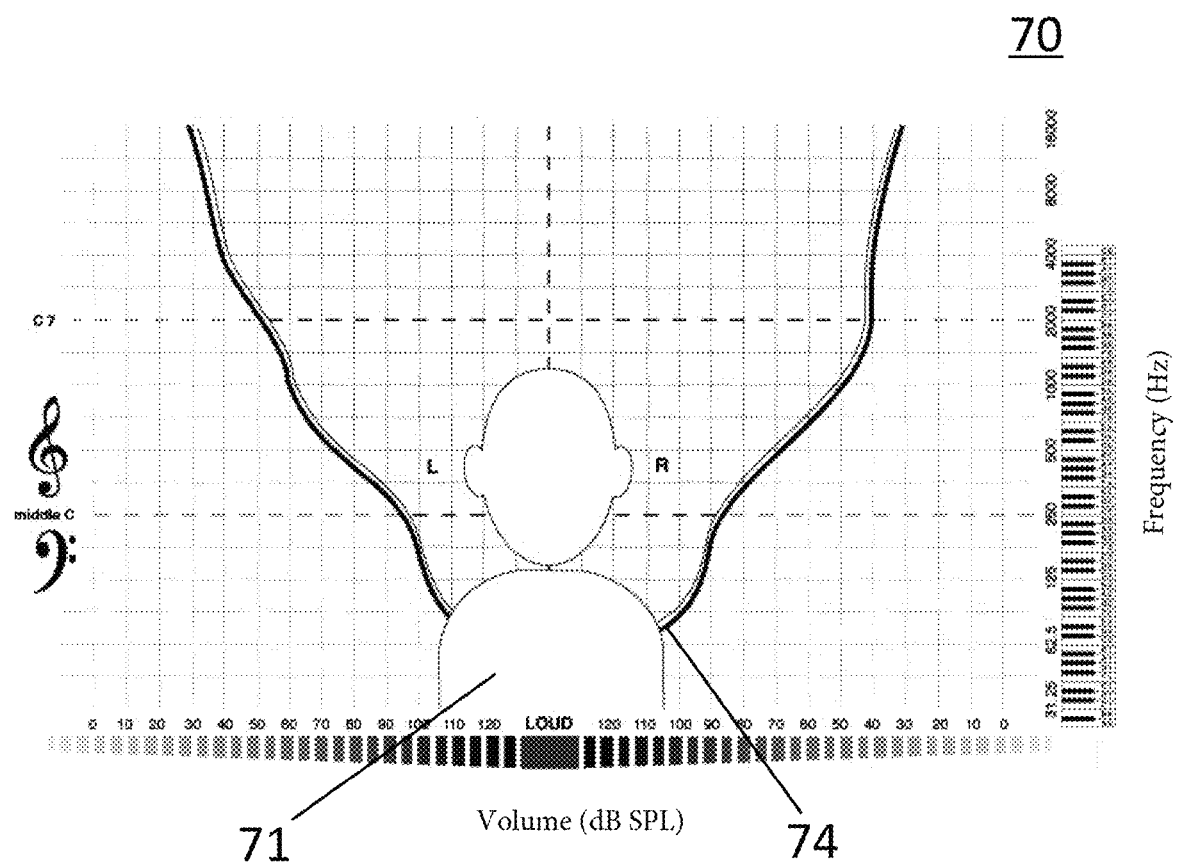
FIG. 8 is a hearing ability visualization that has transformed audiometric data commonly referred to as a "reverse ski slope hearing loss" into an image that may now be referred to as "valley hearing" in accordance with another aspect of the disclosure.

FIG. 8 depicts hearing ability visualization 70 as a graphical visualization that has transformed a commonly called "reverse ski slope hearing loss" into an image similar to walking through a "valley." Because the audiometric data for this type is the reverse of the previous type, i.e., the quantities of decibels heard on each frequency is flipped because the person perceives extremely high frequencies best (shown as 30 dB at 16,000 hz) vs the previous example where the person perceives extremely low frequencies best (shown as 30 dB at 31.25 hz), the resulting visualization is also reversed. Thus, in contrast to hearing ability visualization 60 of FIG. 7, the audiometric data for the lower frequencies is reduced, the "floor" 74 appears visually raised, cutting off the lower parts of the human figure, causing the visualization to start tighter around the human FIG. 71 and widen near the top of the chart, creating the "valley" image.

Example 3

Figure 9:
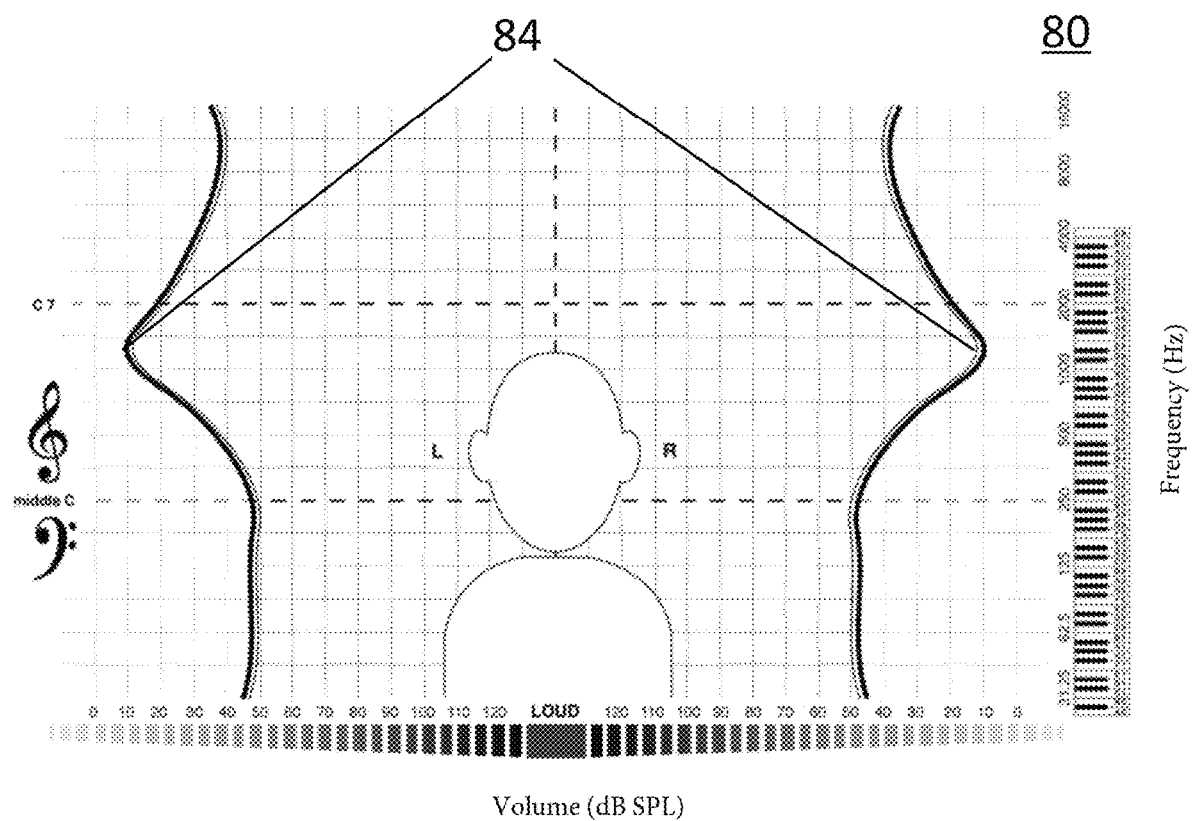
FIG. 9 is a hearing ability visualization that has transformed audiometric data commonly referred to as a "tent hearing loss" into an image that may now be referred to as "curtain hearing" in accordance with another aspect of the disclosure.

FIG. 9 depicts hearing ability visualization 80 as a graphical visualization that has transformed a commonly called "tent hearing loss" into an image similar to walking through a pair of "curtains." With this type of hearing loss there is a "notch" 84 of better hearing in the middle frequency areas, causing the hearing threshold visualization to widen in those parts, as if curtains have been tied back.

Example 4

Figure 10:
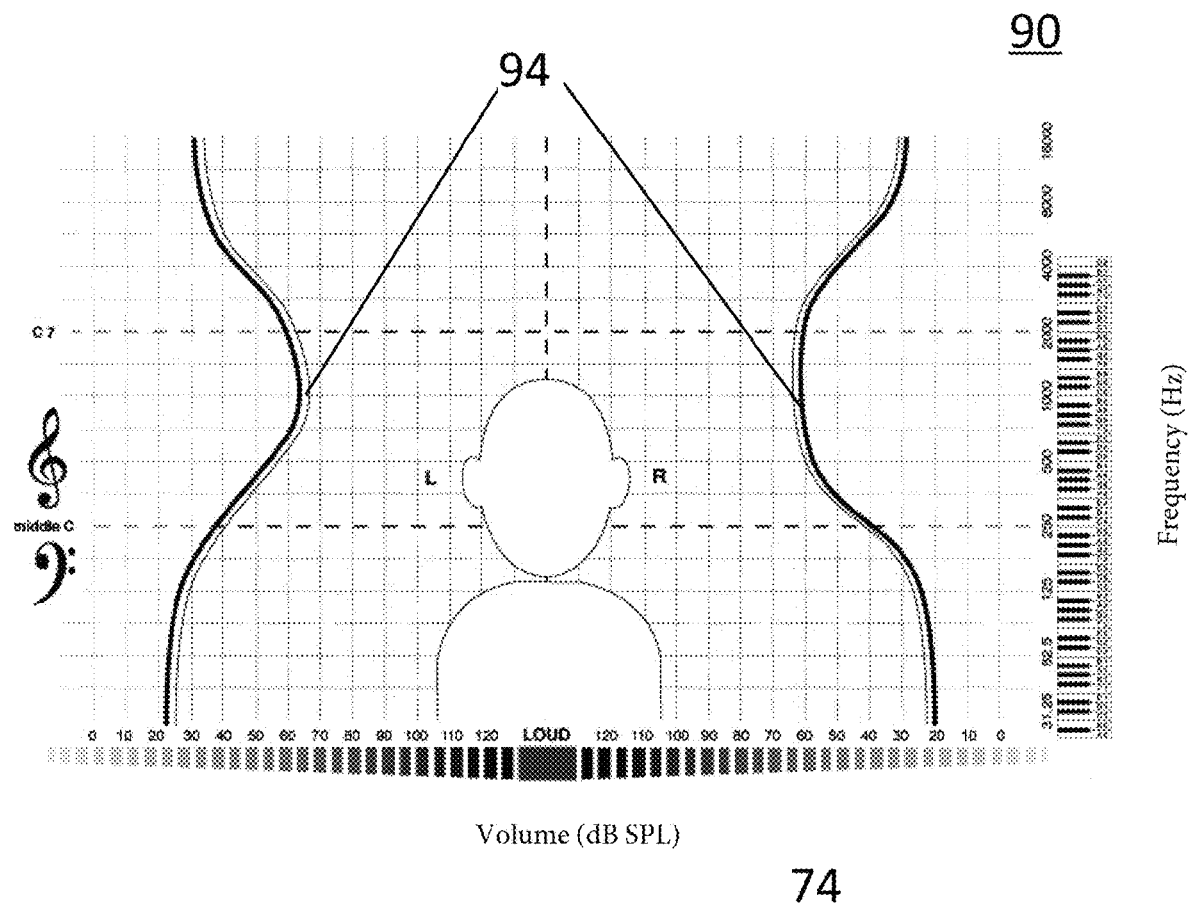
FIG. 10 is a hearing ability visualization that has transformed audiometric data commonly referred to as a "cookie bite hearing loss" into an image that may now be referred to as "canyon hearing" in accordance with another aspect of the disclosure.

FIG. 10 depicts hearing ability visualization 90 as a graphical visualization that has transformed a commonly called "cookie bite hearing loss" into an image that may resemble walking through a "canyon." This type of hearing loss is the rough opposite of the "tent"/"curtain" loss of FIG. 9, in that there is a "bite" 94 of less hearing ability in the middle frequency areas, causing the hearing threshold visualization to bulge in those frequency zones.

Example 5

Figure 11:
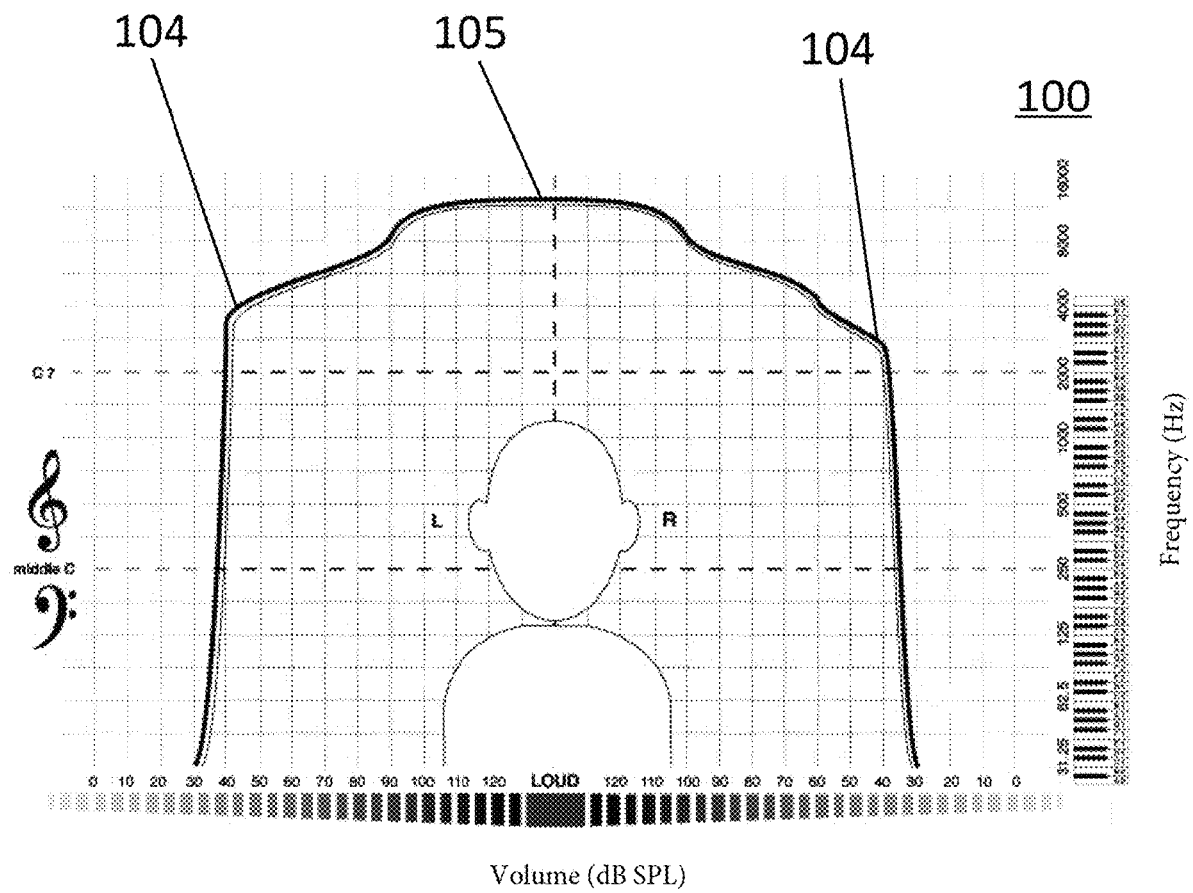
FIG. 11 is a hearing ability visualization that has transformed audiometric data commonly referred to as a "corner hearing loss" into an image that may now be referred to as "archway hearing" in accordance with another aspect of the disclosure.
Figure 12:
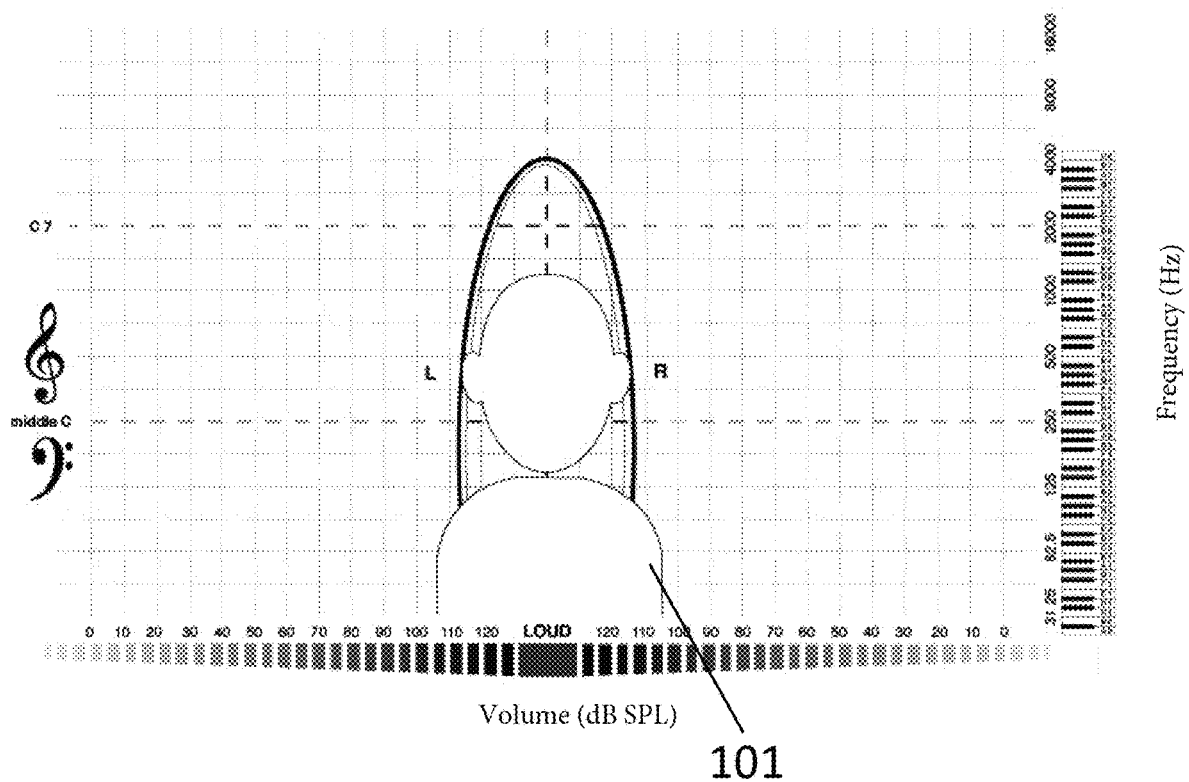
FIG. 12 is a hearing ability visualization that has transformed audiometric data commonly referred to as a "profoundly deaf hearing loss" into an image that may now be referred to as "alley hearing" in accordance with another aspect of the disclosure.

FIG. 11 depicts hearing ability visualization 100 as a graphical visualization that has transformed a commonly called "corner hearing loss" into an image similar to walking under an "arch." On traditional audiograms, this type of loss would be seen as a "corner" crossed off of the grid in either the high or low frequencies. In hearing ability visualization 100, this "corner" 104 is moved to the highest frequencies, creating a slightly lower "ceiling" 105. The angle of the "corner" 104 now may be seen as the lower parts of an archway.

Example 6

FIG. 11 depicts hearing ability visualization 110 as a graphical visualization that has transformed a commonly called "profoundly deaf hearing loss" into an image similar to walking through a narrow "alley." Traditional audiograms visualize this type of hearing ability as a line near the bottom of the chart. Hearing ability visualization 110, however, these previously "bottom" lines are now the tight sides closing in around the human FIG. 101, leaving little to no personal space, as if trying to squeeze through a tight alley.

Flowchart

Figure 13:
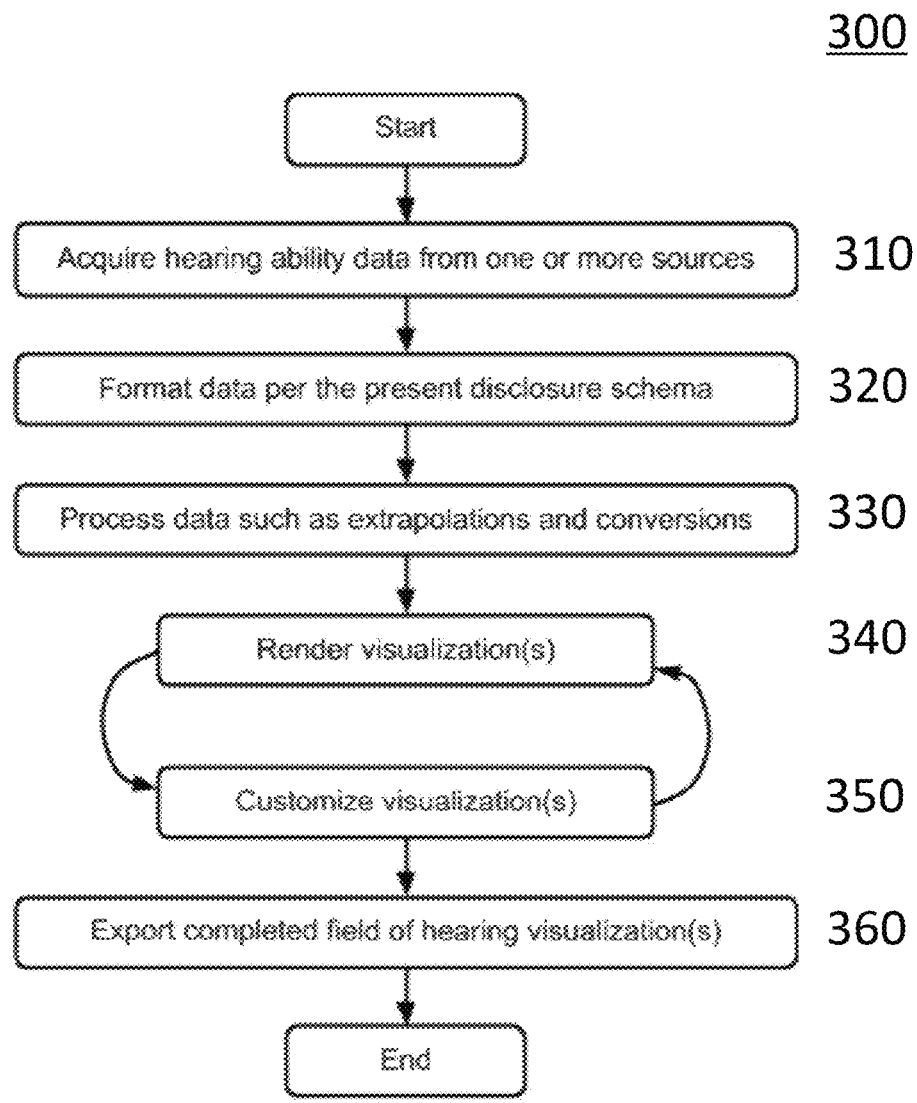
FIG. 13 is a flow chart describing a method for transforming audiometric or other audio data into a hearing ability visualization in accordance with another aspect of the disclosure.

In order to aid comprehension of the present disclosure, the flowchart 300 seen in FIG. 13 is included to describe an exemplary method of producing hearing ability visualizations. Those skilled in the art will recognize this flowchart does not represent the only sequence of steps that may be used for visualizing hearing ability without departing from the scope of the present disclosure in order to achieve the same or similar results. Such methods and approaches include digital embodiments created with or in conjunction with a computing device, such as computing device 200, and/or other audiological equipment. For example, the steps described for flowchart 300 can be stored as instructions in memory module 220 of computing device 200 to be executed by processing module 210.

At start, with reference to step 310, a computing device can acquire audio data, such as audiometric data. Such acquisition may include queries of an existing audiometric database, input from audiometric equipment during an audiology exam, user data transmitted from online hearing tests, manual data entry via a computerized submission form, or through any other means such as scanning a traditional paper audiogram, as seen in FIG. 1, into a computing device.

With reference to step 320, such data may be received at and analyzed by online servers or personal device applications for sorting and formatting. In general, the hearing ability data may be formatted uniformly by converting all volume data into sound pressure level decibels if for example the source data used hearing level decibels and additionally by converting all pitch/frequency data into numbers of hertz if the source data used another pitch/frequency indicator such as musical notes or midi pitch codes. The data may be further sorted by separating left ear/receiver data from right ear/receiver data, and sorting frequency/pitch data with the highest frequency listed first and the lowest frequency listed last. Additional data such as the results of bone conduction tests and auditory reflex tests may also be formatted and sorted accordingly.

With reference to step 330, processing may be conducted after formatting and before rendering the visualization. Such processing can include extrapolating missing data points, estimating the hearing field type based on preliminary data, and conducting further conversions based on the viewing settings. For example, a user may input data from a traditional audiogram that utilized hearing level decibels (dB HL) and also restricted testing to frequencies between 250 hertz to 8,000 hertz, but then wish to supplement this data with additional results from a personal online hearing test to expand the frequencies shown to 20 hz to 20,000 hz but the online test used sound pressure level decibels (dB SPL). In addition, the default viewing settings may be set to a zoom level of the full human hearing spectrum and be requesting a layered visual of the user's cell phone ring in relationship to physical distance from the user. In this scenario, the processing will convert all hearing level decibels into sound pressure level decibels before conducting additional computations of decibels into physical distance using the inverse square law, and then calculate the graphical display by combining the zoom level view with a plot of the cell phone on the underlying hearing visualization zoom grid based on the loudness value of the ringing phone.

With reference to step 340, a visualization may be rendered, such as the mono configuration illustrated in FIG. 2 or the stereo widescreen configuration seen in FIG. 3. The user can select from various modes for the depiction of the audiometric data. For example, a zoom level mode may determine the total width and height of the grid such as a grid large enough to show the totality of possible human hearing ability. A measurement mode may assign values to each point within the grid, such as selecting to view volume as sound pressure level decibels or physical distance in feet. And optional informational graphic elements may be selected and appropriately placed to align with the underlying grid such as the human figure, piano keyboard, and volume meter shown in the exemplary embodiments. The grid itself may or may not be displayed in whole or part, its main purpose is to organize the data in accordance with the present disclosure.

During this visualization process, audiometric data is plotted on the grid and displayed in combination with any modes and/or graphical elements selected. For example, when rendering the example embodiments that utilize a human figure graphical element and the widescreen stereo display mode, the individual data plot points may fill in vertically and horizontally on the left and right sides of the human figure until a sufficient number have been plotted and/or estimated in order to create a visualization of a complete field of hearing. Frequency data may be plotted on the vertical axis with the higher frequencies appearing on the higher parts of the grid and the lower frequencies on the lower parts of the grid. Similarly, the decibel data may be plotted on the horizontal axis with the loudest decibels visualized closer to the location of the entity to which the visualization relates.

For example, with reference to FIG. 2, after acquiring audiometric data, a plot of such data can be generated as an hearing ability visualization 20 with a horizontal axis 23 representing volume (hearing level dB HL, for example) and a vertical axis 22 representing frequency (Hz, for example). Data corresponding to the left ear, represented by line 28, and data corresponding to the left ear, representing line 29, can be plotted with differing visual indicators (e.g., as a dotted line or straight line) to visually distinguish between each type of data. In this mono configuration, lines 28, 29 are plotted on a same side of graphical element 21. Graphical element 21 can act as a reference visually represent the relation of that data to graphical element 21 to provide a visuo-spatial indication of the hearing ability of a patient.

Various lines can be plotted to extend horizontally on hearing ability visualization 20 in relation to graphical element 21 to provide information regarding a patient's hearing ability in relation to certain benchmarks of an average human's hearing ability. For example, line 24 can be plotted to correspond to 250 Hz while line 25 can be plotted to correspond go 2000 Hz, which represents certain commonly heard frequencies. Such lines can be plotted in relation to graphical element 21 (e.g., intersecting graphical element 21) to provide a convenient visuo-spatial understanding of a patient's hearing ability in certain frequency ranges.

In another example, with reference to FIG. 3, hearing ability visualization 30 is similar to hearing ability visualization 20 except graphical element 31 can be placed in a central position along the horizontal axis to be used as a frame of reference for the audiometric data. Such a central position, as previously stated, can represent the volume at which an average human can suffer pain or damage to the ear drums. In this configuration, audiometric data for a left ear can be plotted to a corresponding left side of graphical element 31 to represent the audiometric data for the left ear of a patient while audiometric data for a right ear can be plotted to a corresponding right side of graphical element 31 to represent the audiometric data for the right ear of a patient. The shape of this plot, as described above, can provide a more detailed visuo-spatial indication of the hearing capacity of a patient over traditional audiograms.

In other exemplary methods, the audiometric data can be rendered in a three-dimensional plot. In such embodiments, additional spatial data points regarding hearing perception at the front and back of the entity's location may be acquired and visualized accordingly by plotting this additional spatial data along a third axis representing the physical distance from a centralized graphical element (e.g., graphical element 21, 31). To complete the visualization, the plotted data points may then be linked using a variety of graphical means to delineate the zone of hearing ability surrounding the entity versus the zone outside of the entity's hearing ability and then displayed in 3D on virtual reality and augmented reality display platforms.

With reference to step 350, after completing the initial field of hearing ability visualization, the user may customize and interact with it in a variety of ways, and such interactions may loop back through the above described steps of acquisition 310, formatting 320, processing 330, and rendering 340. For example, the user may adjust the various modes and display options, turn on or off informational graphics, input additional data, import and layer multiple fields of hearing, and import and visualize the benefits of various assistive listening devices and treatment options. In one example, a user may zoom in or out of certain portions of the plot. For example, a user may interact with computing device to zoom into a certain range of frequencies to better view the hearing ability of a patient along that frequency.

With reference to step 360, at any point in the render-customization loop, the resulting image may be exported, printed, and/or saved, thus providing patients, audiologists, researchers, and other interested parties with a completed field of hearing visualization as desired. For example, the hearing ability visualization of this disclosure can be displayed after the plot is generated and subsequent to steps 310-360. However, in other embodiments, the hearing ability visualization can be displayed during the generation step such that the hearing ability visualization is displayed as it's being generated.

In a further step, the computing device can automatically recognize a type of hearing ability of a patient based on the audiometric data and then visually label the plot with a type of hearing ability stored in the computing device based on that audiometric data. For example, the plot can represent one of the plots shown in FIGS. 7-12 and label the plot with acceptable terms for that hearing ability type such as suggested in the examples given, i.e., "cave" hearing and "curtain" hearing and so forth.

The invention claimed is:

1. A computer-implemented method of visualizing hearing ability, comprising:
   acquiring, by one or more processors, audio data; and
   generating, by the one or more processors, a hearing ability visualization with the audio data for display, wherein the hearing ability visualization includes a graphical element, a horizontal axis representing volume, and a vertical axis representing frequency, the graphical element being positioned relative to the horizontal axis such that volume is louder closer to the graphical element and quieter further from the graphical element.

2. The computer-implemented method of claim 1, wherein generating the hearing ability visualization includes plotting a first line intersecting the graphical element and corresponding to a first frequency, and a second line a distance from the graphical element and corresponding to a second frequency, wherein the second frequency is less than the first frequency.

3. The computer-implemented method of claim 2, wherein the second line does not intersect the graphical element.

4. The computer-implemented method of claim 1, wherein the graphical element is placed at a position along the horizontal axis to correspond to a volume level that causes pain to an average human.

5. The computer-implemented method of claim 1, wherein the audio data includes spatial data, wherein generating the hearing ability visualization includes generating a three-dimensional hearing ability visualization with a third axis corresponding to a distance from the graphical element using the spatial data.

6. The computer-implemented method of claim 1, wherein the graphical element is a representation of a human figure.

7. The computer-implemented method of claim 1, wherein the vertical axis is a piano keyboard in which each note of the piano keyboard is in vertical alignment with its corresponding frequency value in hertz.

8. The computer-implemented method of claim 1, wherein the horizontal axis is one of a physical distance, sound pressure level decibels, or hearing level decibels.

9. The computer-implemented method of claim 1, further comprising zooming on a portion of the hearing ability visualization.

10. The computer-implemented method of claim 1, further comprising labelling the hearing ability visualization with a label corresponding to a type of hearing ability based on the audio data.

11. A computer-implemented method of visualizing hearing ability, comprising:
    acquiring, by one or more processors, a first audio data corresponding to a first ear of a patient and a second audio data corresponding to a second ear of a patient; and
    generating, by the one or more processors, a hearing ability visualization with the first and second audio data for display, wherein the hearing ability visualization includes a graphical element, a horizontal axis representing volume, and a vertical axis representing frequency, the first and second audio data being along a same side of the graphical element.

12. The computer-implemented method of claim 11, wherein generating the hearing ability visualization includes plotting a first line intersecting the graphical element and corresponding to a first frequency, and a second line a distance from the graphical element and corresponding to a second frequency, wherein the second frequency is less than the first frequency.

13. The computer-implemented method of claim 12, wherein the second line does not intersect the graphical element.

14. The computer-implemented method of claim 11, wherein the graphical element is placed at a position along the horizontal axis to correspond to a volume level that causes pain to an average human.

15. The computer-implemented method of claim 11, wherein the first and second audio data includes spatial data, wherein generating the hearing ability visualization includes generating a three-dimensional hearing ability visualization with a third axis corresponding to a distance from the graphical element using the spatial data.

16. The computer-implemented method of claim 11, wherein the graphical element is a representation of a human figure.

17. The computer-implemented method of claim 11, wherein the vertical axis is a piano keyboard in which each note of the piano keyboard is in vertical alignment with its corresponding frequency value in hertz.

18. The computer-implemented method of claim 11, wherein the horizontal axis is one of a physical distance, sound pressure level decibels, or hearing level decibels.

19. The computer-implemented method of claim 11, further comprising zooming on a portion of the hearing ability visualization.

20. The computer-implemented method of claim 11, further comprising labelling the hearing ability visualization with a label corresponding to a type of hearing ability based on the first and second audio data.

\* \* \* \* \*